(12) United States Patent  (10) Patent No.: US 7,648,037 B2
Ohashi                     (45) Date of Patent:    Jan. 19, 2010

(54) LID STRUCTURE OF REAGENT CONTAINER

(75) Inventor: Naoki Ohashi, Shizuoka (JP)

(73) Assignee: Olympus Corporation, Tokyo (JP)

( * ) Notice: Subject to any disclaimer, the term of this patent is extended or adjusted under 35 U.S.C. 154(b) by 79 days.

(21) Appl. No.: 12/025,379

(22) Filed: Feb. 4, 2008

(65) Prior Publication Data

US 2008/0296297 A1    Dec. 4, 2008

Related U.S. Application Data

(63) Continuation of application No. PCT/JP2006/315323, filed on Aug. 2, 2006.

(30) Foreign Application Priority Data

Aug. 4, 2005    (JP) .............................. 2005-226997

(51) Int. Cl.
  *B65D 43/26* (2006.01)
  *B65D 51/18* (2006.01)
  *B65D 41/04* (2006.01)
(52) U.S. Cl. ................. 215/313; 215/301; 220/253; 220/254.9; 220/255; 220/262; 220/281
(58) Field of Classification Search ................. 215/313, 215/301; 220/253, 254.8, 254.9, 255, 262, 220/281
See application file for complete search history.

(56) References Cited

U.S. PATENT DOCUMENTS

| 1,577,235 | A | * | 3/1926 | Hucks ........................ 222/363 |
| 1,982,917 | A | * | 12/1934 | Lothrop et al. ......... 222/153.09 |
| 3,703,249 | A |   | 11/1972 | Middleton |
| 5,275,298 | A | * | 1/1994 | Holley et al. ................ 215/11.4 |
| 6,032,813 | A | * | 3/2000 | Niermann et al. ........... 215/312 |
| 6,152,189 | A | * | 11/2000 | Wright et al. .................. 141/2 |
| 6,161,712 | A | * | 12/2000 | Savitz et al. ................ 215/312 |
| 2002/0023892 | A1 | * | 2/2002 | Savitz et al. ................ 215/312 |

FOREIGN PATENT DOCUMENTS

| EP | 0 901 826 A2 | 3/1999 |
| GB | 448119 | 6/1936 |
| JP | 51-146981 | 12/1976 |
| JP | 62-52147 | 4/1987 |
| JP | 10-99302 | 4/1998 |
| JP | 11-171218 | 6/1999 |
| JP | H11-194132 | 7/1999 |
| JP | 2006-189346 | 7/2006 |

* cited by examiner

*Primary Examiner*—Anthony Stashick
*Assistant Examiner*—Niki M Eloshway
(74) *Attorney, Agent, or Firm*—Scully, Scott, Murphy & Presser, P.C.

(57) ABSTRACT

A lid structure for opening and closing an opening in an upper portion of a reagent container includes an outer lid member attached to the reagent container and having a first opening corresponding to the opening of the reagent container, an inner lid member arranged inward of the outer lid member, attached to the outer lid member in a vertically movable manner, and having a second opening opposing the first opening, and a rotator having a through hole, arranged inward of the inner lid member, engaging with the outer lid member and the inner lid member via an engaging unit in a rotatable manner around a horizontal axis. The engaging unit rotates the rotator to open the opening when the inner lid member performs a downward opening operation, and rotates the rotator to close the opening when the inner lid member performs an upward closing operation.

4 Claims, 12 Drawing Sheets

LID STRUCTURE OF REAGENT CONTAINER

CROSS-REFERENCE TO RELATED APPLICATIONS

This application is a continuation of PCT international application Ser. No. PCT/JP2006/315323 filed Aug. 2, 2006 which designates the United States, incorporated herein by reference, and which claims the benefit of priority from Japanese Patent Application No. 2005-226997, filed Aug. 4, 2005, incorporated herein by reference.

BACKGROUND OF THE INVENTION

1. Field of the Invention

The present invention relates to a lid structure for opening and closing an opening formed in an upper portion of a reagent container which holds a reagent inside.

2. Description of the Related Art

Conventionally, a reagent container which holds a reagent for biological analysis is generally kept in a closed state in which an opening formed in an upper portion of the reagent container is covered by a sealing member so that an undesirable event such as evaporation of the reagent can be prevented. When the reagent is used for the analysis, the sealing member is peeled off from the reagent container so that the opening is brought into an open state. The reagent container is placed in a predetermined analyzer, and a probe is inserted inside the reagent container through the opening.

However, once peeled off from the above-described reagent container, the sealing member cannot cover the opening again. As a result, the reagent remaining in the reagent container is disposed. Thus, regardless of a remaining amount of the reagent in the reagent container, the reagent is disposed after each analysis.

To alleviate such inconvenience, a lid structure is proposed to allow for an opening/closing of the opening of the reagent container. After the reagent container is placed in a predetermined analyzer, the lid structure is made to engage with a structural member of the analyzer. Then, the lid structure moves horizontally (laterally) in accordance with the movement of the reagent container, so as to open and close the opening of the reagent container (see, for example, Japanese Patent Application Laid-Open No. H11-194132).

SUMMARY OF THE INVENTION

A lid structure according to one aspect of the present invention is for opening and closing an opening formed in an upper portion of a reagent container holding a reagent inside, and includes an outer lid member that is attached to the reagent container and has a first opening corresponding to the opening of the reagent container, an inner lid member that is arranged inward relative to the outer lid member, attached to the outer lid member in a vertically movable manner, and has a second opening opposing the first opening, and a rotator that has a through hole and is arranged inward relative to the inner lid member, engaging with each of the outer lid member and the inner lid member via an engaging unit in a rotatable manner around a horizontal axis, wherein the engaging unit rotates the rotator to makes the first opening and the second opening communicate with each other through the through hole to bring the opening into an open state when the inner lid member performs a downward opening operation, whereas the engaging unit rotates the rotator to cut the communication between the first opening and the second opening to bring the opening into a closed state when the inner lid member performs an upward closing operation.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
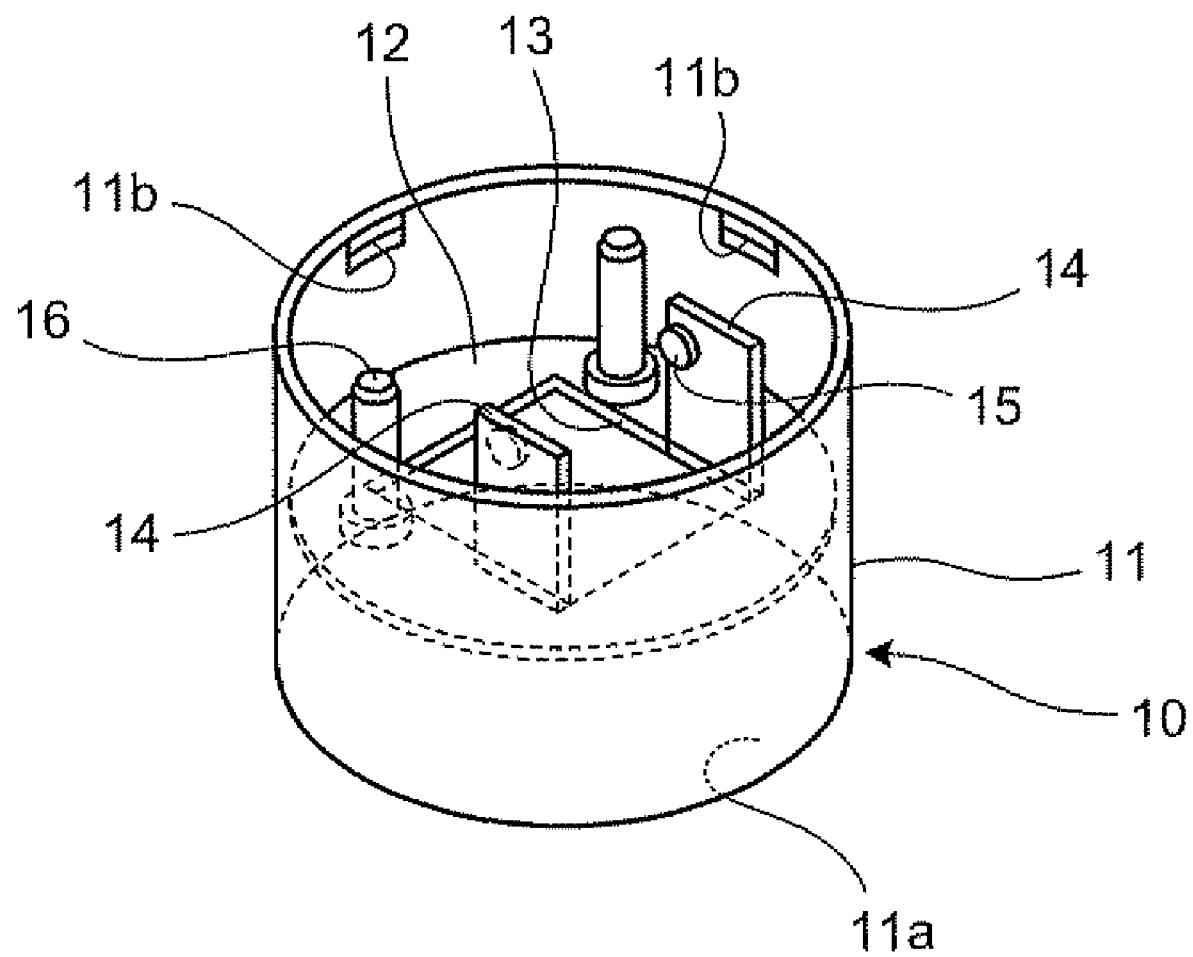
FIG. 1 is a perspective view of an outer lid member which forms a part of a lid structure of a reagent container according to one embodiment of the present invention.

Exemplary embodiments of a lid structure of a reagent container (hereinbelow, the lid structure of the reagent container may be referred to simply as lid structure) according to the present invention will be described in detail below with reference to the accompanying drawings.

FIGS. 1 to 6 show the structure of a lid structure according to one embodiment of the present invention. A reagent container 1 employed herein is a conventionally known container in which a reagent used for biological analysis is put in advance. The reagent container 1 has an opening 2 in an upper portion.

As shown in the drawings, the lid structure includes an outer lid member 10, an inner lid member 20, and a rotating drum (rotator) 30.

Figure 2:
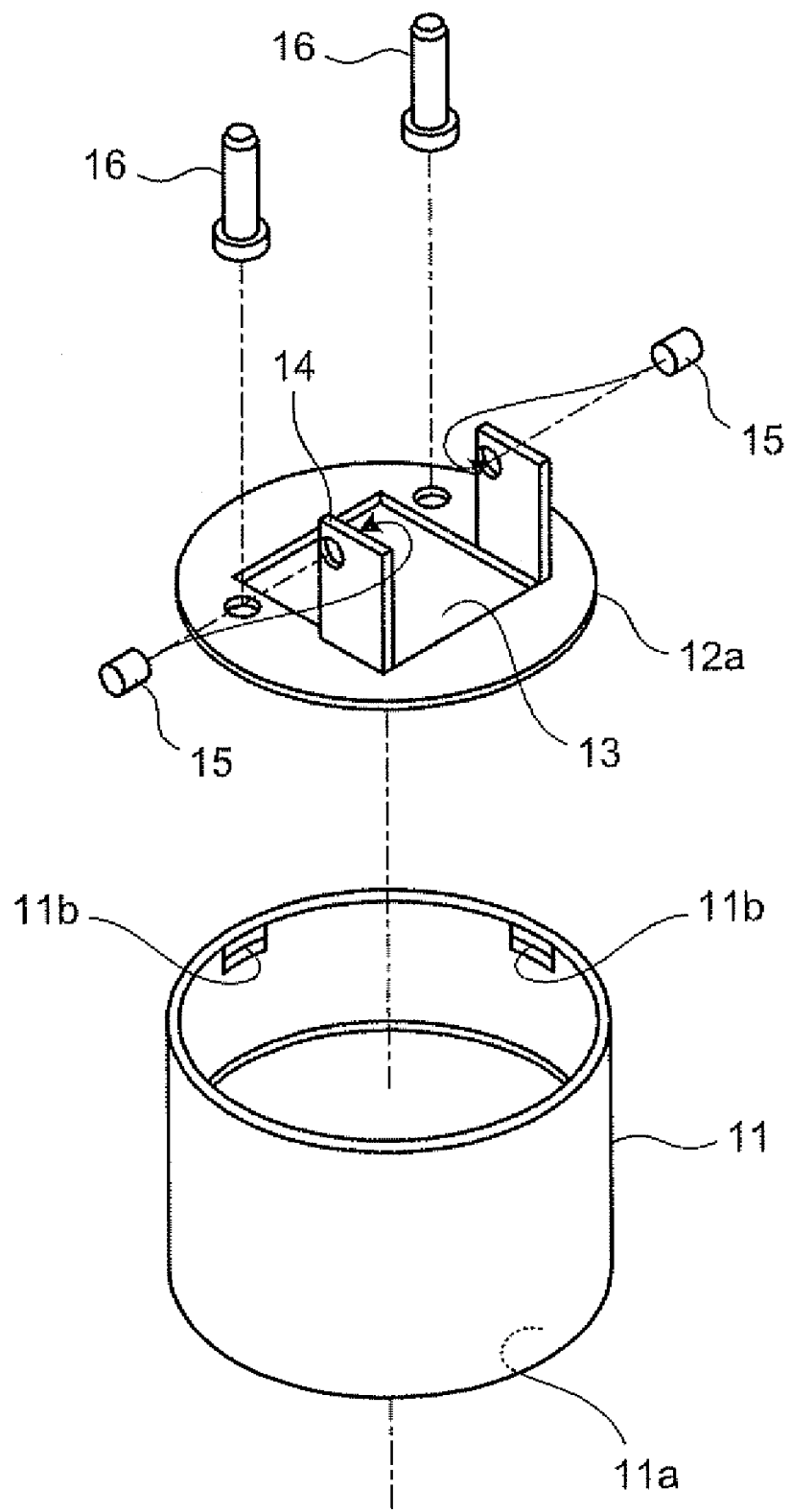
FIG. 2 is an exploded perspective view of the outer lid member shown in FIG. 1.

The outer lid member 10 is made, for example, of a resin material such as plastic. As shown in FIGS. 1 and 2, the outer lid member 10 includes an outer lid main body 11 and a base plate 12. The outer lid main body 11 is cylindrical in shape. In the lower portion of the outer lid main body 11, a fitting portion 11a is formed to be fitted to an upper portion of the reagent container 1 (see FIG. 6). The outer lid main body 11 additionally has retainers 11b on an inner circumference of an upper edge portion to retain the inner lid member 20.

The base plate 12 has a disk-like shape whose outer diameter is substantially the same with the inner diameter of the outer lid main body 11. The base plate 12 is arranged inside the outer lid main body 11 so that the fitting portion 11a is below the base plate 12. More specifically, an end surface 12a of the base plate 12 is bonded to an inner surface of the outer lid main body 11. The base plate 12 has a rectangular first opening 13 in the center. The first opening 13 corresponds to the opening 2 of the reagent container 1. Further, on the base plate 12, a pair of engaging plates 14 are arranged so as to project upward from the first opening 13. Engaging pins 15 are formed on mutually-opposing surfaces of the respective engaging plates 14 so as to face with each other. Further, plural rods 16 are arranged on the base plate 12 so as to project upward (there are two rods 16 in the embodiment). A coil spring (pressing member) is wound around each rod 16 though not explicitly shown.

Figure 3:
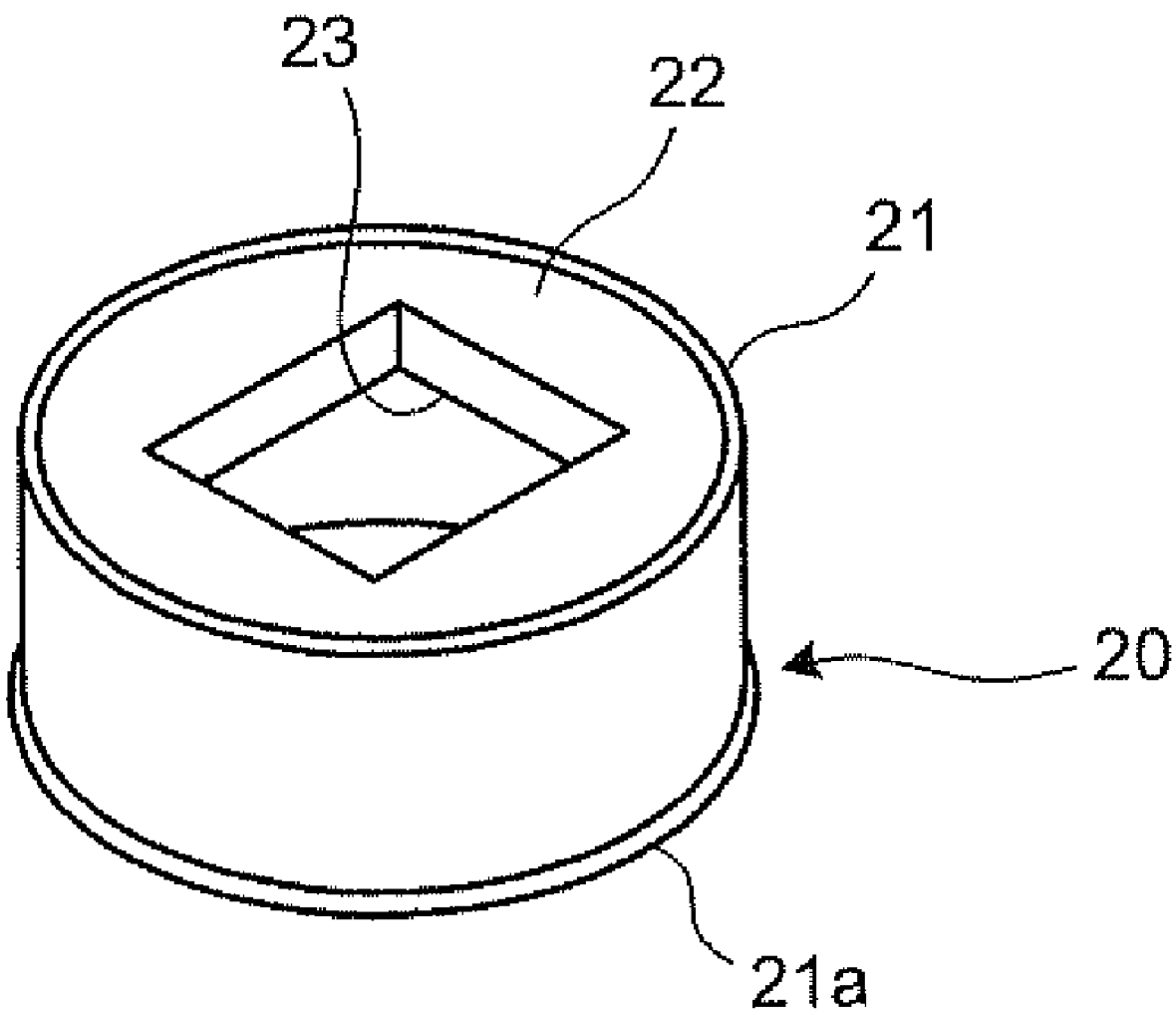
FIG. 3 is a perspective view of an inner lid member which forms a part of the lid structure of the reagent container according to one embodiment of the present invention.
Figure 4:
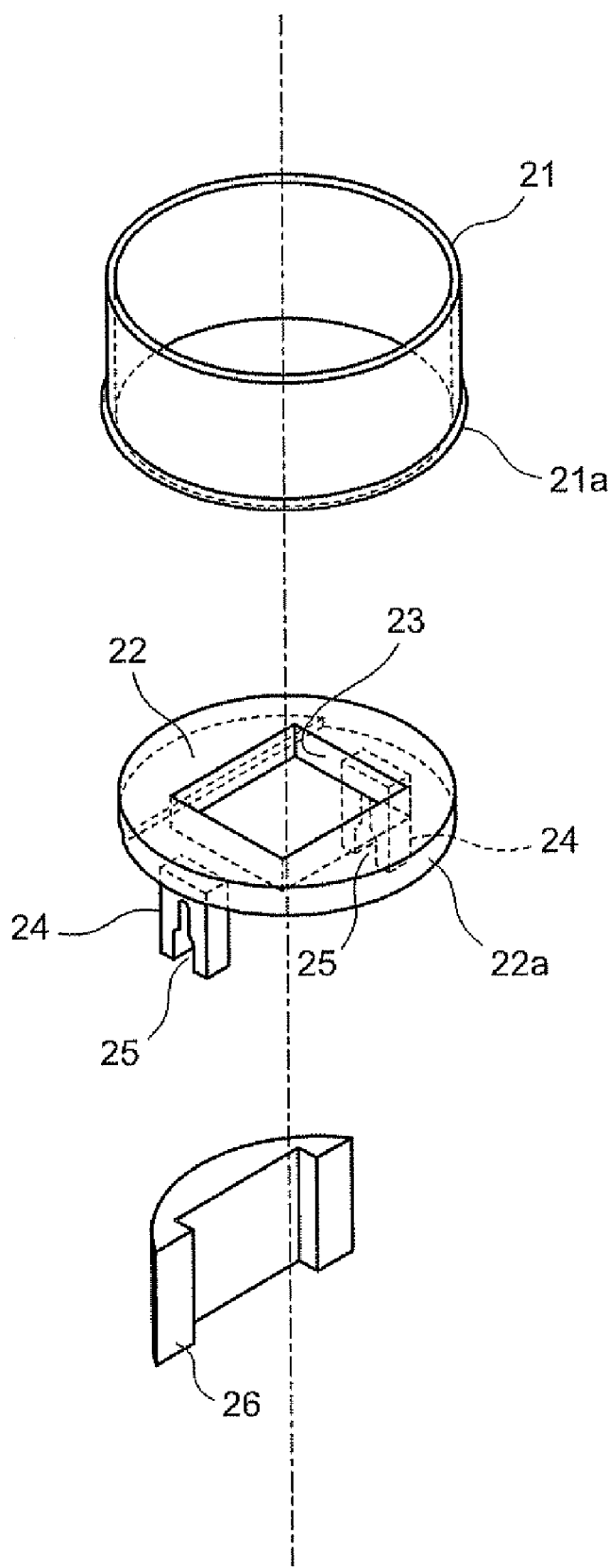
FIG. 4 is an exploded perspective view of the inner lid member shown in FIG. 3.

The inner lid member 20 is made of a resin material such as plastic similarly to the outer lid member 10. As shown in FIGS. 3 and 4, the inner lid member 20 has an inner lid main body 21 and a top plate 22. The inner lid main body 21 is cylindrical in shape though having a smaller diameter than the outer lid member 10 (more specifically, the outer lid main body 11). On an outer circumference of a lower edge portion, a stopper 21a is formed along a circumferential direction and projects radially outward. The stopper 21a, which will be described in detail later, serves to restrict the movement of the inner lid member 20 by abutting against the retainer 11b of the outer lid member 10.

The top plate 22 has a disk-like shape having an outer diameter which is substantially the same as the inner diameter of the inner lid main body 21. The top plate 22 is arranged inside the inner lid main body 21 at an upper end portion thereof. More specifically, an end surface 22a of the top plate 22 is bonded to the inner surface of the upper end portion of the inner lid main body 21. The top plate 22 has a rectangular second opening 23 in the center. The second opening 23 is arranged opposite to the first opening 13 of the outer lid member 10, and the detail will be described later. Further, the top plate 22 has a pair of support plates 24 projecting downward from the second opening 23. Each of the support plates 24 has a cutout 25 widening downward on the lower edge. Further, a spacer 26 is fitted to the top plate 22 so as to project downward similarly to the support plate 24.

Figure 5:
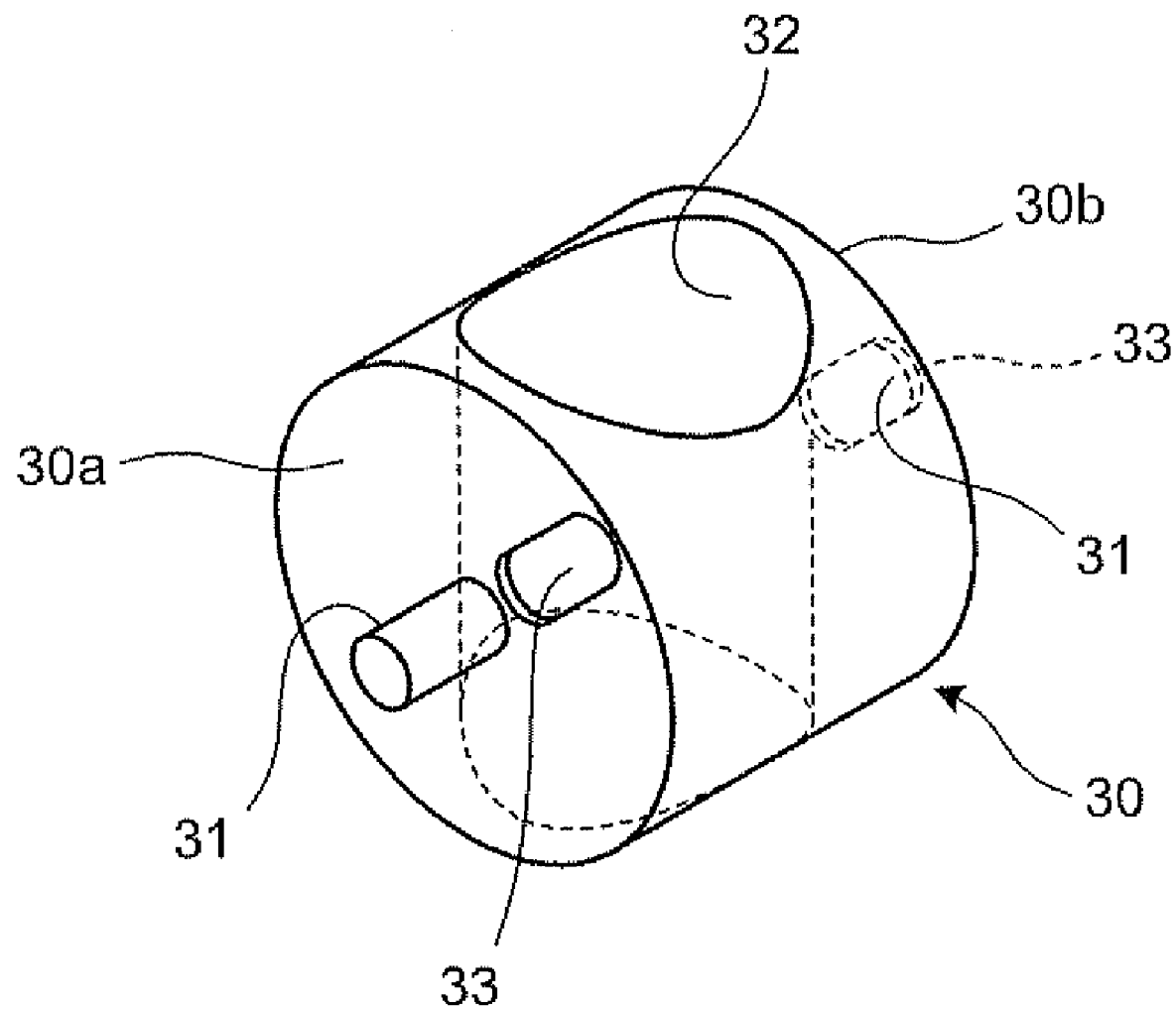
FIG. 5 is a perspective view of a rotating drum which forms a part of the lid structure of the reagent container according to one embodiment of the present invention.

The rotating drum 30 is made, for example, of a resin material such as plastic, and has a substantially columnar shape as shown in FIG. 5. In the rotating drum 30, a support pin 31 is arranged so as to project along a central axis of the rotating drum 30 from each of end surfaces 30a and 30b. The outer diameter of the support pin 31 is such that it fits to the width of the cutout 25 of the support plate 24 of the inner lid member 20. Further, in the rotating drum 30, a through hole 32 is formed in a direction perpendicular to the central axis, in other words, in a vertical direction of FIG. 5. On the end surfaces 30a and 30b of the rotating drum 30, oval engaging grooves 33 are formed respectively to extend in the same radially outward direction from the support pin 31. The width of the engaging groove 33 is such that it fits to the outer diameter of the engaging pin 15 of the engaging plate 14 of the outer lid member 10.

Figure 6:
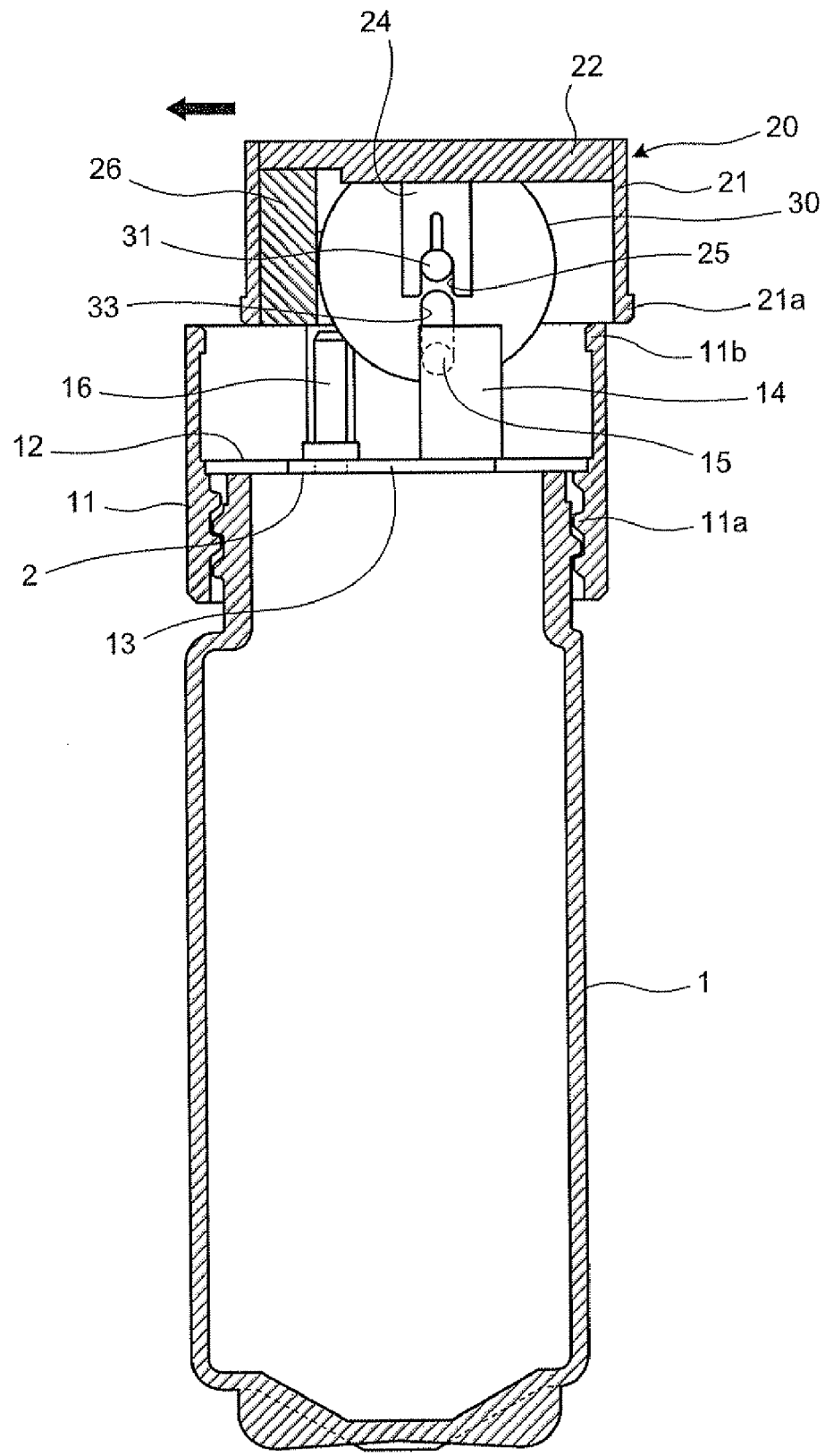
FIG. 6 is a schematic sectional side view of the lid structure according to one embodiment of the present invention in a fitted state.

FIG. 6 is a schematic sectional side view of the lid structure according to one embodiment of the present invention in a fitted state. FIG. 6 will be referred to as appropriate in the description of the lid structure.

Firstly, the outer lid member 10 is fitted to the reagent container 1 with the fitting portion 11a fitted onto the upper portion of the reagent container 1. The base plate 12 is arranged at an open end of the reagent container 1 so that the first opening 13 of the base plate 12 corresponds to the opening 2 of the reagent container 1. The outer lid member 10 may be detachable from the reagent container 1.

Figure 7:
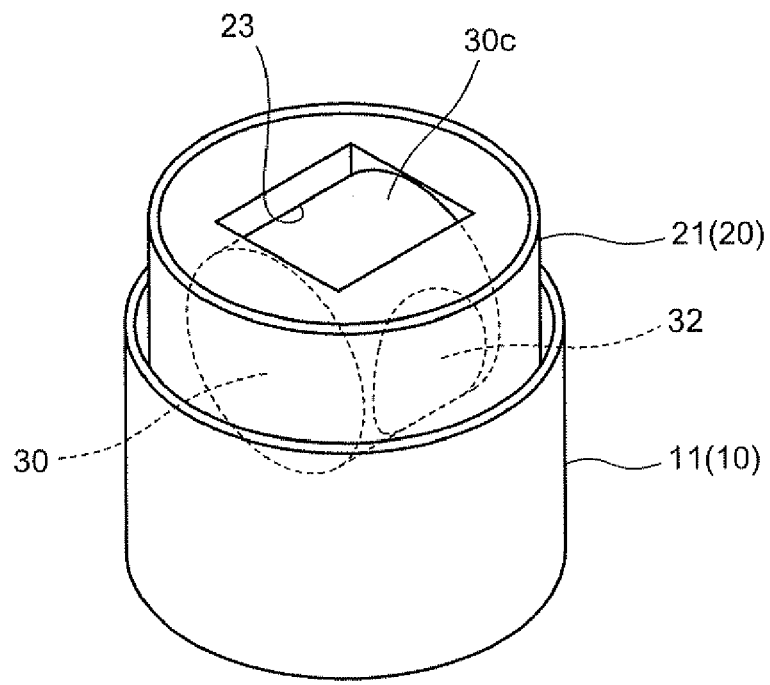
FIG. 7 is a perspective view of the lid structure where the inner lid member is at an top dead center.
Figure 8:
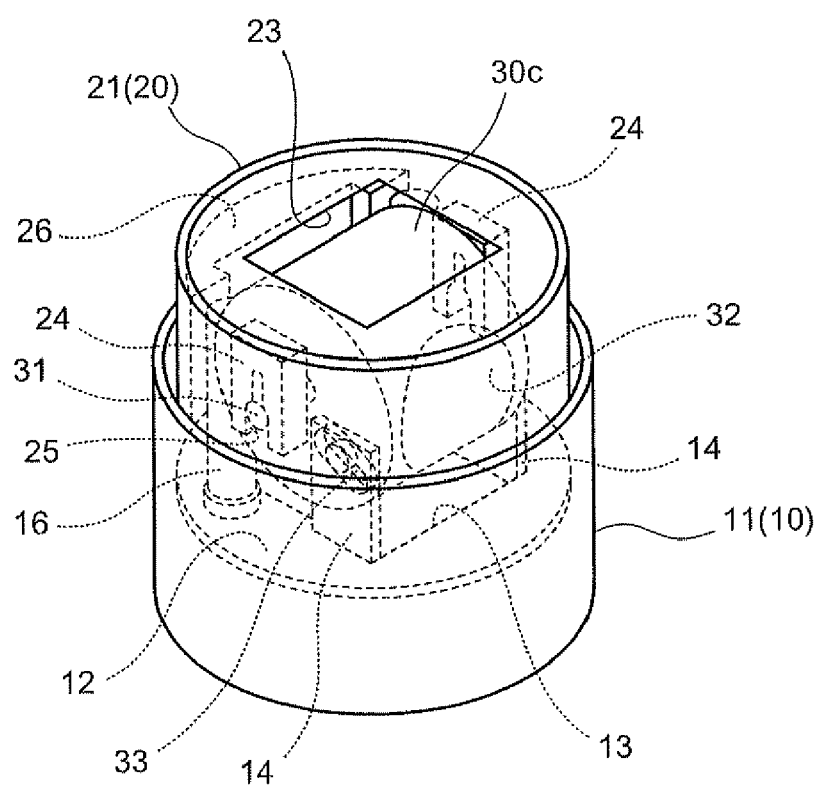
FIG. 8 is a perspective view of an interior of the lid structure shown in FIG. 7.
Figure 9:
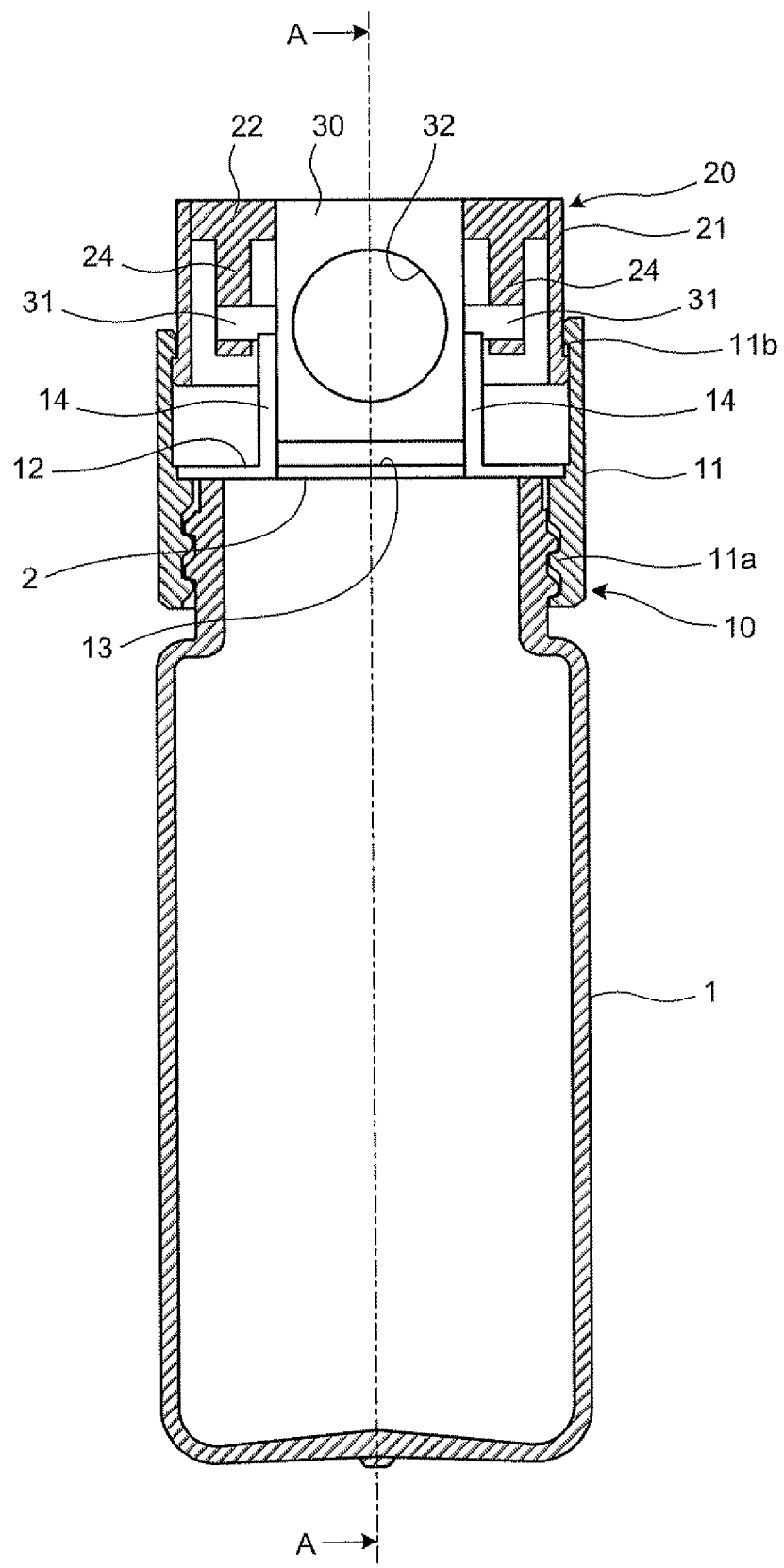
FIG. 9 is a sectional side view of the lid structure shown in FIG. 7.
Figure 10:
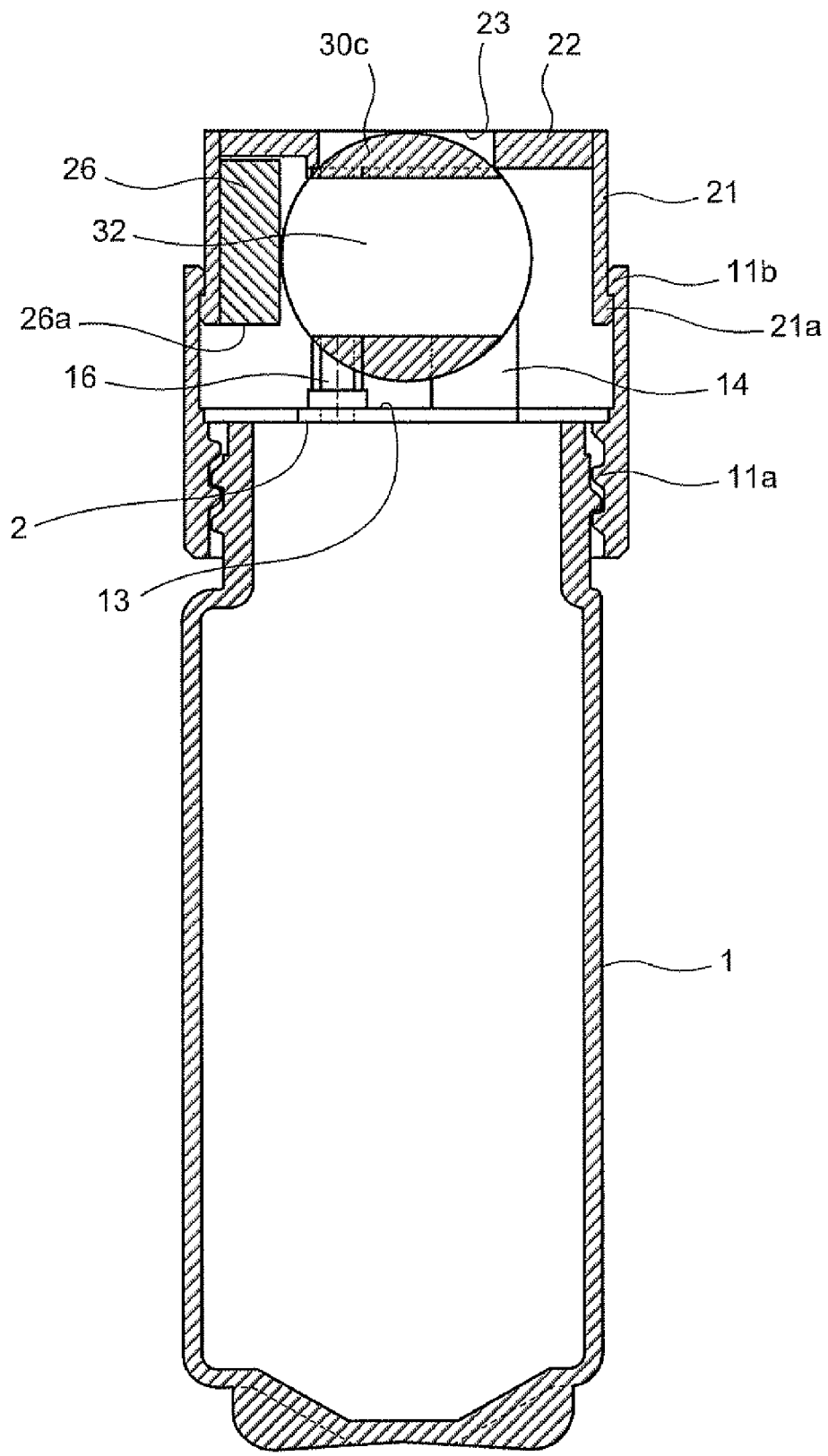
FIG. 10 is a sectional view along line A-A of FIG. 9.

Then, the rotating drum 30 is arranged so that the central axis thereof matches with the horizontal axis, and the engaging pin 15 of the outer lid member 10 is inserted into the engaging groove 33 of the rotating drum 30. Thus, the rotating drum 30 engages with the outer lid member 10. On the other hand, the support pin 31 of the rotating drum 30 is inserted into the cutout 25 of the inner lid member 20 so that the rotating drum 30 engages with the inner lid member 20. The inner lid member 20 is moved in the direction of an arrow of FIG. 6 (i.e., leftward) while the rotating drum 30 remains engaged with the inner lid member 20. Then, the inner lid member 20 is pressed downward so that the inner lid member 20 is inserted into the outer lid member 10. The inner lid member 20 inserted into the outer lid member 10 moves upward due to pressing force of the coil spring wound around the rod 16. The stopper 21a of the inner lid member 20 is brought into contact with the retainer 11b of the outer lid member 10, whereby the inner lid member 20 reaches a top dead center as shown in FIGS. 7 to 10. FIG. 7 is a perspective view of the lid structure when the inner lid member is positioned at the top dead center, FIG. 8 is a perspective view of an interior of the lid structure shown in FIG. 7, FIG. 9 is a sectional side view of the lid structure, and FIG. 10 is a sectional view along line A-A of FIG. 9. Here, the inner lid member 20 may be detachable from the outer lid member 10.

As shown in FIGS. 7 to 10, when the inner lid member 20 is positioned at the top dead center, the through hole 32 of the rotating drum 30 is arranged in the direction of a horizontal axis, and a side circumferential portion 30c of the rotating drum 30 is inserted in the second opening 23 of the inner lid member 20 which opposes to the first opening 13 of the outer lid member 10. Thus, the communication between the first opening 13 and the second opening 23 is cut. In other words, the opening 2 of the reagent container 1 is in a closed state. Further, the engaging groove 33 on each of the end surfaces 30a and 30b of the rotating drum 30 extends in a direction from the central axis of the rotating drum 30 to obliquely downward, radially outward direction.

The lid structure which keeps the opening 2 of the reagent container 1 in a closed state as described above can bring the opening 2 of the reagent container 1 into an open state as follows.

When the inner lid member 20 at the top dead center is pressed and moves downward, in other words, when the inner lid member 20 performs an opening operation against the pressing force of the coil spring, the support pin 31 fitted in the cutout 25 is pressed by the support plate 24. Thus, the rotating drum 30 as a whole moves downward. At the same time, since the outer lid member 10 exerts an upward reactive force via the engaging pin 15 in the engaging groove 33, the engaging pin 15 presses the edge portion of the engaging groove 33 to make the rotating drum 30 rotate around the horizontal axis in the direction of arrow shown in FIG. 6.

Figure 11:
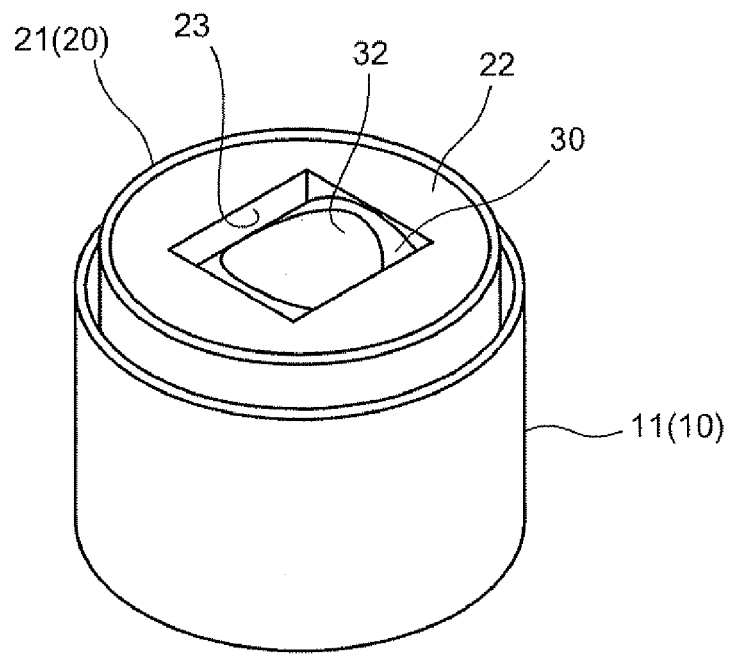
FIG. 11 is a perspective view of the lid structure where the inner lid member is at a bottom dead center.
Figure 12:
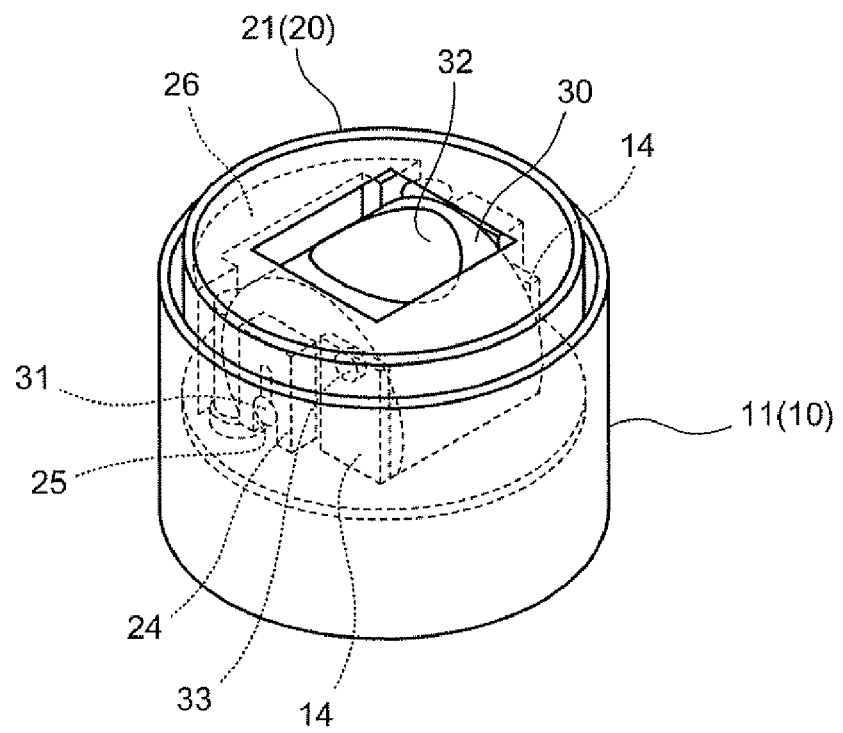
FIG. 12 is a perspective view of an interior of the lid structure shown in FIG. 11.
Figure 13:
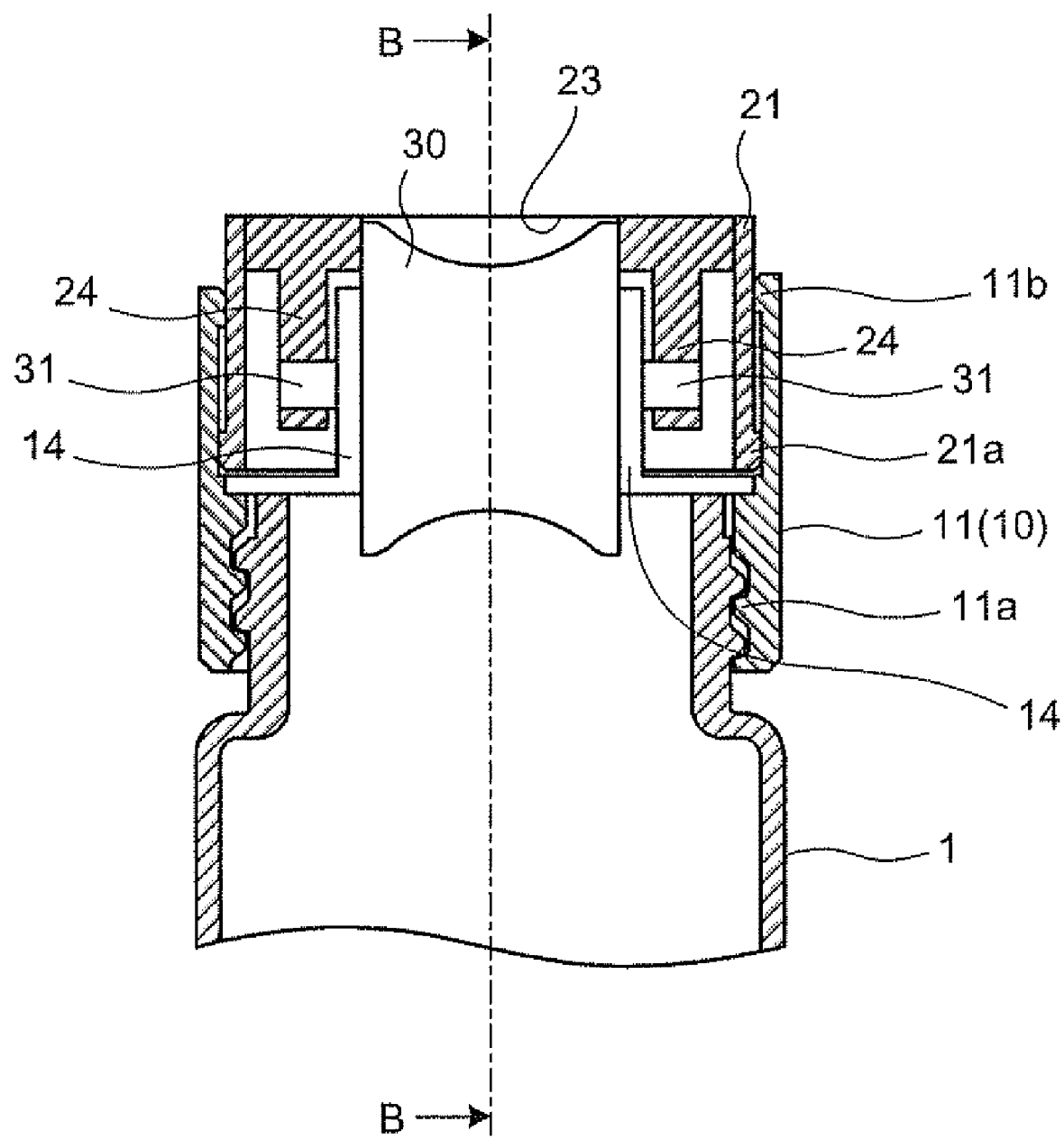
FIG. 13 is a sectional side view of the lid structure shown in FIG. 11.
Figure 14:
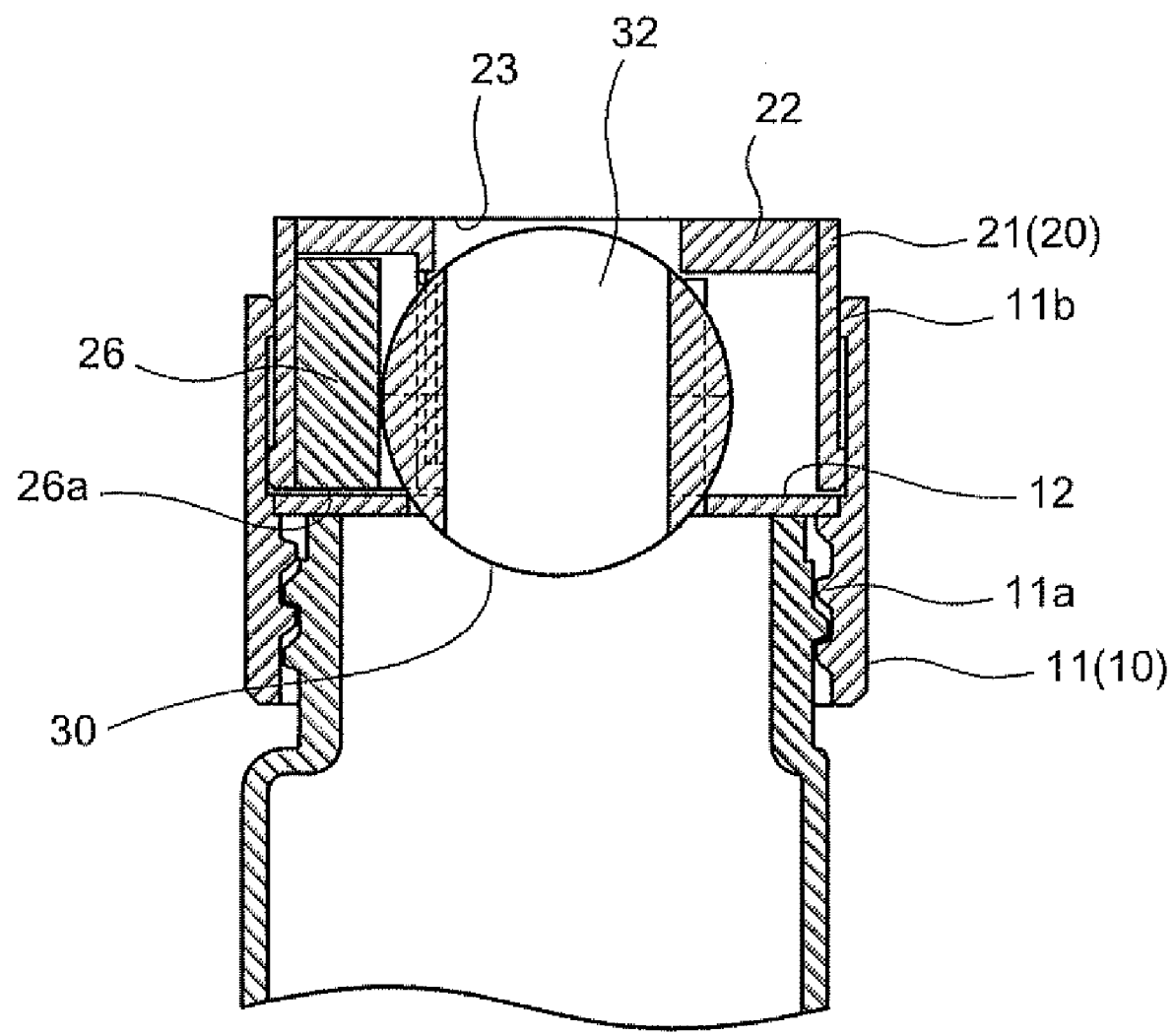
FIG. 14 is a sectional view along line B-B of FIG. 13.

When the through hole 32 of the rotating drum 30 which rotates around the horizontal axis comes to a vertical direction as shown in FIGS. 11 to 14, the lower end surface 26a of the spacer 26 of the inner lid member 20 is brought into contact with the upper surface of the base plate 12 of the outer lid member 10 so as to stop the opening operation of the inner lid member 20. The inner lid member 20 is positioned at a bottom dead center. When the inner lid member 20 is positioned at the bottom dead center, the first opening 13 of the outer lid member 10 and the second opening 23 of the inner lid member 20 are communicated with each other through the through hole 32. Thus, the opening 2 of the reagent container 1 is brought into an open state. FIG. 11 is a perspective view of the lid structure when the inner lid member is positioned at the bottom dead center, FIG. 12 is a perspective view of the interior of the lid structure shown in FIG. 11, FIG. 13 is a sectional side view of the lid structure, and FIG. 14 is a sectional view along line B-B of FIG. 13.

When the inner lid member 20 is released from the pressure, the inner lid member 20 moves upward from the bottom dead center according to the pressing force of the coil spring. In other words, the inner lid member 20 performs a closing operation. When the inner lid member 20 performs the closing operation, the rotating drum 30 as a whole moves upward keeping the support pin 31 engaged with the cutout 25. At the same time, since the outer lid member 10 exerts the downward reactive force via the engaging pin 15 in the engaging groove 33, the engaging pin 15 presses the edge portion of the engaging groove 33 to make the rotating drum 30 rotate around the horizontal axis in an opposite direction from the direction mentioned earlier.

When the stopper 21a of the inner lid member 20 is brought into contact with the retainer 11b of the outer lid member 10 during the closing operation, the inner lid member 20 stops the closing operation and reaches the top dead center (see FIGS. 7 to 11). Then, as described above, the through hole 32 of the rotating drum 30 runs along the direction of the horizontal axis, and the side circumferential portion 30c enters the second opening 23 of the inner lid member 20. Thus, the communication between the first opening 13 and the second opening 23 is cut, and the opening 2 of the reagent container 1 is brought into a closed state. Through the repetitions of the opening operation and the closing operation of the inner lid member 20 as described above, the opening 2 of the reagent container 1 can be opened and closed many times.

In summary, the engaging pin 15 of the outer lid member 10, the engaging groove 33 and the support pin 31 of the rotating drum 30, and the cutout 25 of the inner lid member 20 configure an engaging unit which rotates the rotating drum 30 to make the first opening 13 and the second opening 23 communicated with each other through the through hole 32 and thereby bringing the opening 2 of the reagent container 1 into an open state when the inner lid member 20 performs the opening operation, whereas rotates the rotating drum 30 to cut the communication between the first opening 13 and the second opening 23 to bring the opening 2 into a closed state when the inner lid member 20 performs the closing operation.

When the reagent container 1 having the above-described lid structure is placed in a predetermined analyzer so that a reagent is employed for the biological analysis, an element of the analyzer presses the inner lid member 20 to realize the opening operation, and the rotating drum 30 rotates around the horizontal axis. Then, the inner lid member 20 comes to the bottom dead center, and the second opening 23 of the inner lid member 20 is communicated with the first opening 13 of the outer lid member 10 through the through hole 32, whereby the opening 2 of the reagent container 1 is brought into an open state. Then, a probe or the like is inserted into the reagent container 1 through the opening 2 in the open state so that the reagent can be collected and used for the analysis. Thereafter, the element releases the inner lid member 20 from the pressure to make the inner lid member 20 perform the closing operation according to the pressing force of the coil spring. The rotating drum 30 rotates, and when the inner lid member 20 reaches the top dead center, the communication between the second opening 23 of the inner lid member 20 and the first opening 13 of the outer lid member 10 is cut, whereby the opening 2 of the reagent container 1 is brought into a closed state.

The lid structure according to the embodiment rotates the rotating drum 30 to make the first opening 13 and the second opening 23 communicated with each other via the through hole 32 when the inner lid member 20 performs the downward opening operation so that the opening 2 of the reagent container 1 is brought into an open state, whereas the lid structure rotates the rotating drum 30 to make the communication between the first opening 13 and the second opening 23 cut when the inner lid member 20 performs the upward closing operation so that the opening 2 is brought into a closed state. The vertical movements of the inner lid member 20 can realize the opening and closing of the opening 2. Thus, when the reagent container 1 having the above-described lid structure is placed in a predetermined analyzer, the reagent container 1 can be arranged without any consideration to the space where the inner lid member 20 moves. In particular, the lid structure of one reagent container 1 does not interfere with the lid structure of another adjacent reagent container 1 even when plural reagent containers 1 are placed in the analyzer. Thus, the lid structure of the reagent container according to the present invention is advantageous in that it can open and close the opening 2 of the reagent container 1 with a simple structure and that it has excellent space utilization efficiency.

Further, the above-described lid structure has a smaller number of parts in comparison with the conventional lid structure which moves in the horizontal direction, and cost can be reduced.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A lid structure for opening and closing an opening formed in an upper portion of a reagent container holding a reagent inside, comprising:
    an outer lid member that is attached to the reagent container and has a first opening corresponding to the opening of the reagent container;
    an inner lid member that is arranged inward relative to the outer lid member, attached to the outer lid member in a vertically movable manner, and has a second opening opposing the first opening; and
    a rotator that has a through hole and is arranged inward relative to the inner lid member, engaging with each of the outer lid member and the inner lid member via an engaging unit in a rotatable manner around a horizontal axis, wherein
    the engaging unit rotates the rotator to makes the first opening and the second opening communicate with each other through the through hole to bring the opening into an open state when the inner lid member performs a downward opening operation, whereas the engaging unit rotates the rotator to cut the communication between the first opening and the second opening to bring the opening into a closed state when the inner lid member performs an upward closing operation.

2. The lid structure of a reagent container according to claim 1, further comprising a pressing member that constantly presses the inner lid member upward, wherein the inner lid member performs the opening operation against a pressing force of the pressing member, and performs the closing operation according to the pressing force of the pressing member.

3. The lid structure of a reagent container according to claim 1, wherein the outer lid member is detachably attached to the reagent container.

4. The lid structure of a reagent container according to claim 1, wherein the inner lid member is detachably attached to the outer lid member.

* * * * *